(12) United States Patent
Bulko

(10) Patent No.: US 7,722,735 B2
(45) Date of Patent: May 25, 2010

(54) MICROSTRUCTURE APPLIQUE AND METHOD FOR MAKING SAME

(75) Inventor: John B. Bulko, Franklin, MA (US)

(73) Assignee: C3 Materials Corp., Nashua, NH (US)

( * ) Notice: Subject to any disclaimer, the term of this patent is extended or adjusted under 35 U.S.C. 154(b) by 630 days.

(21) Appl. No.: 11/784,249

(22) Filed: Apr. 6, 2007

(65) Prior Publication Data

US 2007/0243312 A1    Oct. 18, 2007

Related U.S. Application Data

(60) Provisional application No. 60/789,902, filed on Apr. 6, 2006.

(51) Int. Cl.
| | |
|---|---|
| B29C 65/48 | (2006.01) |
| B29C 65/02 | (2006.01) |
| B32B 37/24 | (2006.01) |
| B32B 38/16 | (2006.01) |
| B05D 3/02 | (2006.01) |
| B05D 1/36 | (2006.01) |
| B05D 1/02 | (2006.01) |
| B05D 1/12 | (2006.01) |

(52) U.S. Cl. .............. 156/249; 156/276; 156/279; 156/289; 156/307.3; 156/307.5; 427/2.26; 427/189; 427/191; 427/202; 427/203

(58) Field of Classification Search ................ 156/155, 156/242, 244.21, 247, 249, 276, 278, 279, 156/289, 307.1, 307.3, 307.5; 427/2.24, 427/2.26, 189, 191, 202, 203, 407.1, 414; 419/2, 9, 64, 65

See application file for complete search history.

(56) References Cited

U.S. PATENT DOCUMENTS

| | | | | |
|---|---|---|---|---|
| 3,388,004 | A * | 6/1968 | Rosenblatt | ............... 502/101 |
| 3,605,123 | A | 9/1971 | Hahn | |
| 3,607,369 | A * | 9/1971 | Batta | ...................... 427/309 |
| 3,855,638 | A | 12/1974 | Pilliar | |
| 3,871,200 | A * | 3/1975 | Onoda et al. | ................. 72/41 |
| 3,897,221 | A * | 7/1975 | Salyer et al. | ............ 428/566 |
| 4,017,911 | A * | 4/1977 | Kafesjian et al. | ......... 623/2.35 |
| 4,049,428 | A * | 9/1977 | Elbert et al. | ................. 419/2 |
| 4,073,999 | A * | 2/1978 | Bryan et al. | ........... 428/312.8 |
| 4,101,984 | A * | 7/1978 | MacGregor | .............. 623/2.42 |
| 4,244,824 | A * | 1/1981 | Lange et al. | ......... 210/500.23 |

(Continued)

Primary Examiner—Philip C Tucker
Assistant Examiner—Sing P Chan
(74) Attorney, Agent, or Firm—MacMillan, Sobanski & Todd, LLC

(57) ABSTRACT

A method is described for forming a porous coating on the surface of a substrate such as an implantable prosthesis wherein a microstructure appliqué is made in the shape and depth of the area to be coated, adhesively attached to that area and subsequently bonded to the substrate through the application of an appropriate sintering treatment. Manufacture of the microstructure appliqué is accomplished through the transfer and deposition of one or more packed layers of uniformly-sized, metallic particles onto a shaped pattern followed by the addition of a binder solution for preserving the packing of particles and the integrity of the shaped piece. The method disclosed herein provides a means of making uniform and reproducible structures possessing uniform porosity and is adaptable to automation for producing larger quantities of appliqués, which may help in reducing costs associated with prosthetic implant production.

16 Claims, 3 Drawing Sheets

U.S. PATENT DOCUMENTS

| | | | | |
|---|---|---|---|---|
| 4,357,393 A * | 11/1982 | Tsuda et al. | | 428/547 |
| 4,443,404 A * | 4/1984 | Tsuda et al. | | 419/2 |
| 4,536,894 A | 8/1985 | Galante et al. | | |
| 4,550,448 A | 11/1985 | Kenna | | |
| 4,569,821 A * | 2/1986 | Duperray et al. | | 419/2 |
| 4,612,160 A | 9/1986 | Donlevy et al. | | |
| 4,636,219 A * | 1/1987 | Pratt et al. | | 623/23.3 |
| 4,644,942 A * | 2/1987 | Sump | | 623/23.55 |
| 4,660,755 A * | 4/1987 | Farling et al. | | 228/178 |
| 4,693,864 A * | 9/1987 | Lloyd | | 419/23 |
| 4,702,930 A * | 10/1987 | Heide et al. | | 427/2.27 |
| 4,793,968 A * | 12/1988 | Mosser et al. | | 428/550 |
| 4,846,393 A * | 7/1989 | Devillard | | 228/178 |
| 4,854,496 A * | 8/1989 | Bugle | | 228/193 |
| 5,080,674 A * | 1/1992 | Jacobs et al. | | 623/20.17 |
| 5,104,410 A | 4/1992 | Chowdhary | | |
| 5,236,457 A * | 8/1993 | Devanathan | | 128/898 |
| 5,470,401 A * | 11/1995 | McCallum et al. | | 148/302 |
| 5,504,300 A * | 4/1996 | Devanathan et al. | | 219/121.64 |
| 5,571,187 A * | 11/1996 | Devanathan | | 623/66.1 |
| 5,672,284 A * | 9/1997 | Devanathan et al. | | 219/121.64 |
| 5,734,959 A * | 3/1998 | Krebs et al. | | 419/2 |
| 5,773,789 A * | 6/1998 | Devanathan et al. | | 219/121.64 |
| 5,846,664 A * | 12/1998 | Third et al. | | 428/550 |
| 5,848,351 A * | 12/1998 | Hoshino et al. | | 428/550 |
| 5,926,685 A * | 7/1999 | Krebs et al. | | 419/2 |
| 5,973,222 A * | 10/1999 | Devanathan et al. | | 623/11.11 |
| 6,033,788 A * | 3/2000 | Cawley et al. | | 428/548 |
| 6,049,054 A * | 4/2000 | Panchison et al. | | 219/121.64 |
| 6,087,024 A * | 7/2000 | Whinnery et al. | | 428/613 |
| 6,132,674 A * | 10/2000 | Compton et al. | | 419/2 |
| 6,193,761 B1 | 2/2001 | Treacy | | |
| 6,209,621 B1 | 4/2001 | Treacy | | |
| 6,253,443 B1 * | 7/2001 | Johnson | | 29/557 |
| 6,291,012 B1 * | 9/2001 | Miyasaka | | 427/191 |
| 6,514,288 B2 * | 2/2003 | Meulink et al. | | 623/23.3 |
| 6,544,472 B1 * | 4/2003 | Compton et al. | | 419/2 |
| 6,652,804 B1 * | 11/2003 | Neumann et al. | | 419/2 |
| 6,656,526 B2 * | 12/2003 | Pan | | 427/243 |
| 6,663,688 B2 * | 12/2003 | Findeisen et al. | | 75/252 |
| 6,740,186 B2 * | 5/2004 | Hawkins et al. | | 156/242 |
| 6,814,928 B2 * | 11/2004 | Sagawa et al. | | 419/38 |
| 6,838,046 B2 * | 1/2005 | Lu et al. | | 419/5 |
| 6,840,978 B2 * | 1/2005 | Matsuura et al. | | 75/240 |
| 6,939,509 B2 * | 9/2005 | Kochanek | | 419/36 |
| 6,945,448 B2 * | 9/2005 | Medlin et al. | | 228/248.1 |
| 7,014,712 B2 * | 3/2006 | Sano et al. | | 118/209 |
| 7,241,415 B2 * | 7/2007 | Khoshnevis | | 419/6 |
| 7,296,990 B2 * | 11/2007 | Devos et al. | | 425/375 |
| 7,597,715 B2 * | 10/2009 | Brown et al. | | 623/22.32 |
| 7,632,575 B2 * | 12/2009 | Justin et al. | | 428/615 |
| 2002/0168282 A1 * | 11/2002 | Lu et al. | | 419/54 |
| 2003/0037639 A1 * | 2/2003 | Findeisen et al. | | 75/236 |
| 2003/0054149 A1 * | 3/2003 | Pan | | 428/292.1 |
| 2004/0137209 A1 * | 7/2004 | Zeller et al. | | 428/304.4 |
| 2005/0149170 A1 * | 7/2005 | Tassel et al. | | 623/1.15 |
| 2006/0003179 A1 * | 1/2006 | Wang et al. | | 428/613 |
| 2006/0105015 A1 * | 5/2006 | Perla et al. | | 424/423 |
| 2007/0243312 A1 * | 10/2007 | Bulko | | 427/2.1 |
| 2008/0106853 A1 * | 5/2008 | Suenaga | | 361/529 |

\* cited by examiner

MICROSTRUCTURE APPLIQUE AND METHOD FOR MAKING SAME

CROSS-REFERENCE TO RELATED APPLICATIONS

This application claims the benefit of U.S. Provisional Application No. 60/789,902, filed Apr. 6, 2006, the disclosure of which is incorporated herein by reference.

BACKGROUND OF THE INVENTION

The invention relates to a method of forming a porous structure on the surface of a solid substrate. The porous structure is created by the use of a microstructure appliqué consisting of a binder and a particulate material formed in the predetermined shape and depth and applied to a substrate of similar or dissimilar material and geometrical configuration. The process is especially, although not exclusively, useful for making prosthetic implant devices with porous metal-coated surfaces.

Various methods have been disclosed in the literature for providing a porous metal coating on the surfaces of prosthetic implants for securing such devices by means of both soft and hard (bone) tissue ingrowth.

In one such method disclosed by Hahn in U.S. Pat. No. 3,605,123, a porous surface structure is built up by applying multiple metal layers using a flame spray process. This technique was found to be undesirable due to the weak interfacial adhesion to bone tissue. Later techniques by Pillar (in U.S. Pat. No. 3,855,638) and others (see patent references) formed the porous metal coating on implant devices by applying a slurry of metallic powder suspended in aqueous solution with organic binders. The applied slurry layer is converted to the porous coating through diffusion bonding of the metallic particles to one another and to the substrate surface, thereby creating substantially uniform pores and pore size distribution. In U.S. Pat. No. 4,017,911, Kafesjian teaches a method where an adhesive is applied to select areas of a valve body casting followed by pouring metallic powder of specific size onto the treated areas. Additional layers of powder are applied by repeating the process until reaching the desired thickness. After achieving the desired depth, the coated casting is sintered in an appropriate atmosphere to permanently attach the particles to the casting and to each other. The shape and size of the metallic powder and the appropriate choice of sintering conditions control the porosity of the sintered layer.

In U.S. Pat. No. 4,536,894 by Galante et al, the application of prefabricated porous pads secured to flat surfaces or pressed into hollow depressions on the stem of a hip prosthesis is mentioned but no method is given for fabricating the porous pads.

Porous coatings are again added to bone prosthesis in U.S. Pat. No. 4,550,448 where a layer of spherical metal powder is deposited on adhesive-coated areas, via treatment in a fluid bed, and presintered to burn off the binder and establish bonding between different particles and between particles and the substrate surface. A second layer of particles is added on top of the first layer in similar fashion and presintered a second time for establishing secure bonding between layers. A third sinter step is performed on the coated substrate to promote formation of secure junctions between particles, between layers and attachments to the substrate. Several drawbacks to using such a method involving multiple high-temperature heat treatments would be the addition of significant time and costs to the manufacturing cycle as well as the potential to degrade both mechanical properties and material properties and distort prosthesis dimensions.

Yet in another method called out in U.S. Pat. No. 4,612,160, a porous metal coating is created by positioning a rigid mold in close proximity to a substrate such that the space between mold and substrate defines the boundaries of the porous layer. The defined space is filled with metal powder, without a binder, and the mold/substrate assembly then presintered to lightly bind particles together and to the substrate. After removal from the mold, the coated substrate is further sintered to obtain the proper desired bond strength and pore volume. This technique would be difficult to implement for coating areas with complex geometrical shapes and patterns but offers a way to eliminate sources of contamination introduced through the use of adhesive binders. In a related method, Bugle, in U.S. Pat. No. 4,854,496, describes a method where a porous pad of pure titanium is first made by presintering powder in a cavity of the desired shape. The shaped pad then sintered to achieve required bond strength, the pad flattened on one side to create a bonding surface and finally sintered to the substrate under application of pressure within a non-reactive atmosphere.

Chowdhary describes a method in U.S. Pat. No. 5,104,410 wherein a titanium powder is combined with a urea to form a mixture that is compressed into pockets using a hydraulic press. After compaction, the urea component is leached out of the pressed-on material by soaking the device in water and subsequently dried and sintered in vacuum. The porosity of the added layer is created by the removal of urea within the volume of the compacted pockets.

In a series of patents by Devanathan et al, the inventor describes the application and fixation of porous surfaces to an implant using laser welding. In U.S. Pat. No. 5,773,789, porous metal pads are fabricated using a sintering or diffusion bonding process. Pre-shaped pads with adhesive backing are placed on the implant and coupled to the surface at a plurality of locations by application of a laser beam to form weld beads attaching the pads to the implant body.

Finally, metallic porous bead preforms are described in U.S. Pat. Nos. 6,193,761 and 6,209,621. Here, the bead preforms are first prepared by mixing metallic beads with binder, such as methylcellulose, and applying the resultant slurry to a mold of the desired shape. The bead/binder slurry is fired to burn off the binder and bond beads together. The shaped preform is then attached to the prosthesis during its formation by the casting of molten metal into a refractory shell containing said preform positioned where a porous metal coating is desired on the implant device.

SUMMARY OF THE INVENTION

The present invention enables the production of devices with porous metal-coated surfaces possessing uniform and reproducible pore diameters and volume. This is accomplished preferably by the utilization of microstructure appliqués that are manufactured in specific shape and controlled dimension and positioned at locations on a surface where a porous coating is desired.

In carrying out the present method, microstructure appliqués are fabricated according to the prescribed series of steps. The shape of the appliqué is formed to correspond to the shape of a selected area where a porous coating is to be applied. A pattern of the representative shape is cut out from a suitable substrate material such as silicone rubber. Then, through a series of repetitive actions, multiple layers of uniformly sized and packed particles are transferred to and retained on the pattern with application of an appropriate binder solution. After attaining the desired thickness, the appliqué is removed from the pattern and adhesively attached to the area of corresponding shape. The above process can be used to specifically make structures consisting of only one layer of particles by executing the series of steps one time. Permanent attachment of the appliqué to the surface, as it relates to prosthetic implant devices, is accomplished through the application of an appropriate sintering treatment under controlled conditions.

The advantages of the present invention include a method of making uniform and reproducible structures with uniform porosity in controlled shapes and thickness that can be applied to prosthetic implant surfaces for establishing porous metal coatings into which bone tissue can infiltrate and grow. The method is adaptable to automation such that microstructure appliqués of specific shape and dimension can be produced in large quantity, thereby shortening the manufacturing cycle and reducing costs associated with prosthetic implant production. The scope of the porous microstructure appliqués shall not be limited to the sole application for medical implant devices and can be used to apply porous coatings used elsewhere in such areas as filtration, separations and fluid processing technologies.

The object of this invention is to provide a method for applying particulate particles on a substrate for the purpose of making a porous surface structure.

A further object is to provide a means whereby the particulate material can be formed into microstructure appliqués that may be adhered to the substrate.

A further object is to provide a means of reducing production time and costs by reducing the number of steps to manufacture prosthetic implant devices having porous metal coatings.

A further object is to provide a more uniform and reproducible means of packing the particles within the porous surface structure of the prosthetic implant.

A further object is to provide a means for controlling both shape and depth of a porous surface structure applied to a prosthetic implant.

A further object is to provide a means for controlling a uniform size of pores within the porous surface structure by using a narrow distribution of particle sizes.

This invention features a method of making microstructure appliqués that can accommodate a plurality of vaporizable binder systems which thermally decompose without leaving objectionable residues or contaminants within the porous structure.

This invention results from the realization that a vaporizable binder and particulates can be formed into flexible structures that can be handled, through appropriate selection of binder, processing and forming, for preparing porous coatings on the surface of prosthetic implants.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT

Figure 1:
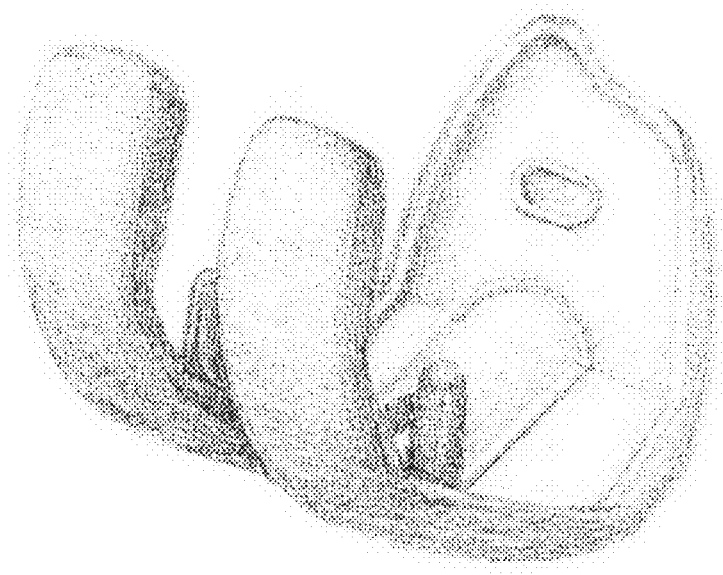
FIG. 1 is drawing of a femoral knee component showing the interior surfaces where a porous metal coating is typically applied.
Figure 2:
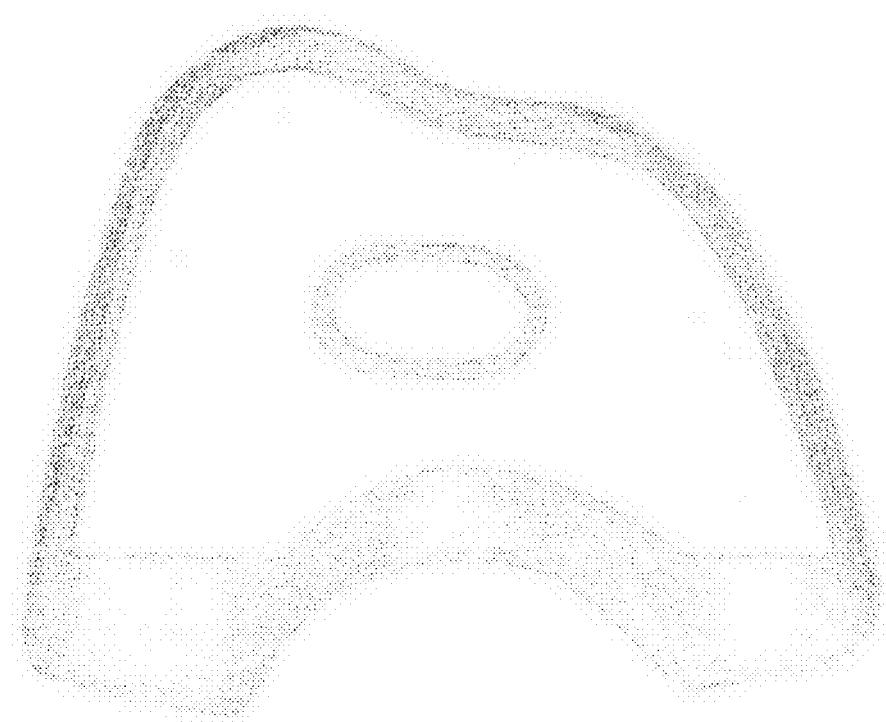
FIG. 2 is a drawing of the upper end section of the femoral knee component depicting an area with curved perimeter and an oval-shaped border in the center.
Figure 3:
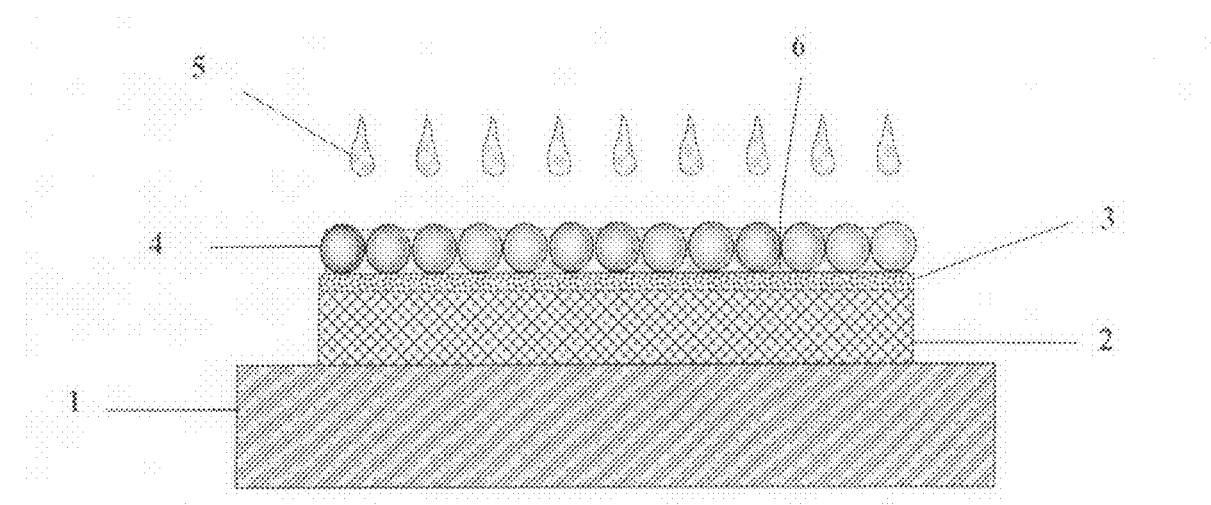
FIG. 3 is a side view of the microstructure appliqué consisting of one layer of metal powder particles 4 adhered to a silicone rubber pad 2 by application of an adhesive layer 3 and held together through the addition of a binder solution 5 and filling the space in-between particles 6.
Figure 4:
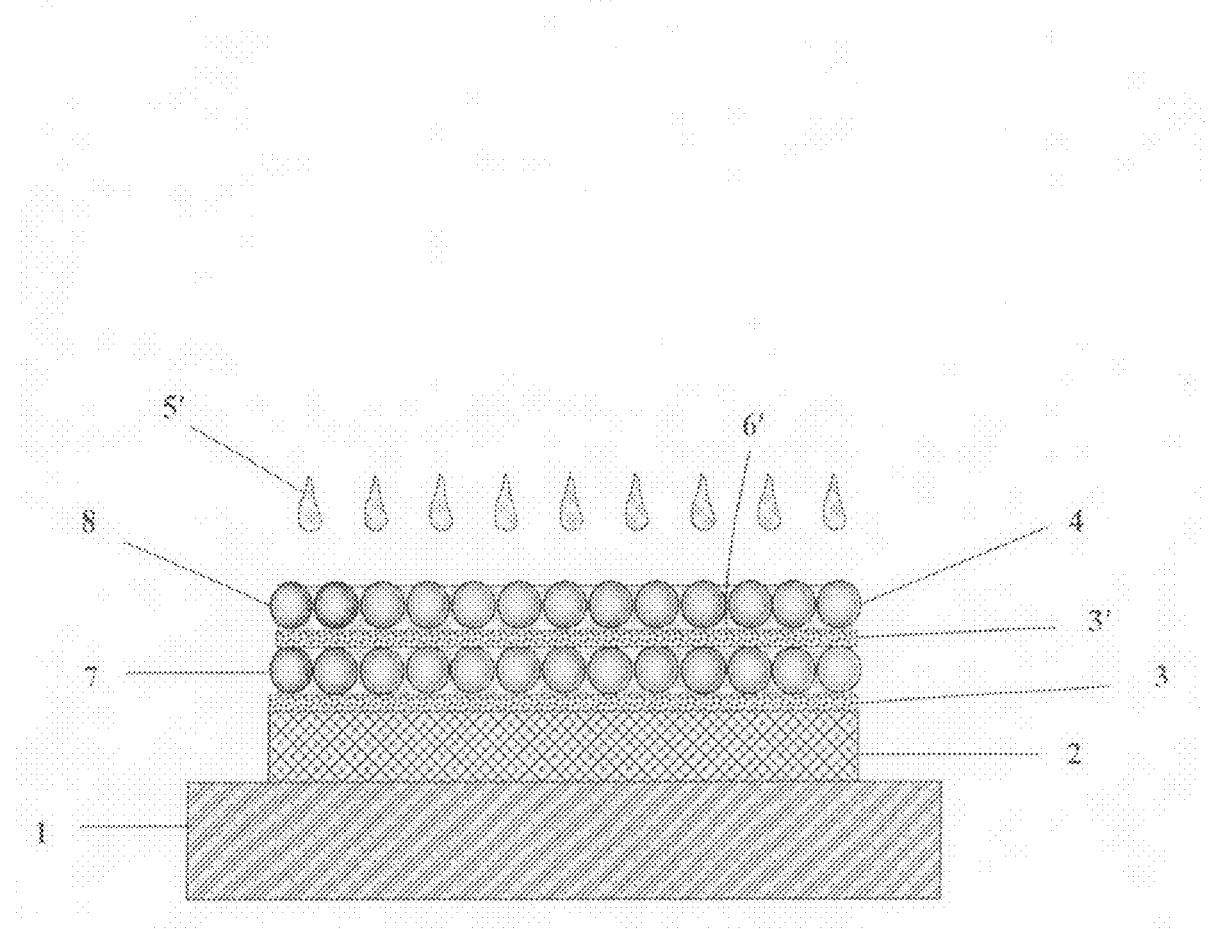
FIG. 4 is a side view of a microstructure appliqué consisting of two layers of metal powder particles adhered to the silicone rubber pad 2 showing the addition of a second adhesive layer 3' and second layer of powder particles 8 over the first layer 7 and addition of more binder solution 5' to fill the space between particles in the second layer 6'.

The invention will be described in detail using FIGS. 3 and 4 as an outline. The specific shape of the microstructure appliqué corresponds to a section of a femoral knee component shown in FIG. 2.

The process for making a microstructure appliqué starts by loading metal powder of the desired particle size into a shallow trough or tray such that the powder forms a dense, closely-packed body of particles at a depth of one particle diameter (mono-layer). Packing of the powder particles can be assisted by intermittent tapping of the tray or by the addition of mechanical vibration until the particles reach a maximum desired packing density in a single layer.

The shape of the microstructure appliqué is formed to correspond to the shape of a selected region of the prosthesis where a porous metal coating is to be situated. The desired shape is cut from a sheet of silicon rubber of suitable firmness (60 A durometer) and possessing an adhesive layer on one side such that the shaped rubber cut-out can be adhered to a support block 1 suitable for mounting in a hand operated or air-actuated press.

Once the shaped pad 2 is mounted on the support block, a thin layer of adhesive 3 with sufficient tackiness is sprayed (via aerosol) onto the pad surface and allowed to stand for a minute to develop maximum tackiness. A suitable product for this application is Repositionable 75 Spray Adhesive (3M, St. Paul, Minn.) although others may be used.

The support block 1 with mounted pad 2 is then situated in the air-actuated press or like device such that the pad surface covered with adhesive is parallel to and facing the trough of packed powder particles. The pad/support block is pressed onto the single layer of packed particles with enough force to capture and transfer essentially all of those particles coming into contact with the adhesive layer 3. Contact between pad and tray is typically maintained for a period of 5-10 seconds. The press is used here only as a means of maintaining the pad parallel to the packed layer of particles in the tray and ensures contact between pad surface and particles is uniform and reproducible.

The pad/support block with captured particles is then removed from the press and reoriented to a horizontal position with the powder layer facing upward. A binder solution 5 is then applied to the packed powder surface in sufficient quantity to fill the void volume 6 between particles in such a manner as to not disturb the particle packing. The preferred means for addition of the binder solution 5 is accomplished with the use of an airbrush or similar device that dispenses the binder solution in the form of micro-droplets. The support block 1 containing the pad 2 with applied powder 4 and binder solution 5 is then placed in an oven at 70° C. for 15-30 minutes to accelerate the curing of the binder.

After the single layer of powder particles with binder has matured sufficiently, the thickness of the microstructure appliqué may be adjusted by adding additional layers of particles of like size or different sizes. Typical porous metal coatings can range from 2 to 4 layers in thickness, depending upon the type and application of the prosthesis. This can be accomplished by repeating the steps to form a second layer, beginning with preparing another single layer of powder particles in the tray and applying another layer of aerosol spray adhesive 3' over the surface of assembled particles 7 covering the shaped silicon rubber pad 2, as shown in FIG. 4. The support block 1 with pad 2 and first layer of metal particles 7 is then pressed onto the packed layer of particles in the trough to pick up a second layer of particles 8 onto the first layer 7. After reorienting the support block and pad to the horizontal position, additional binder solution 5' is applied to the packed particle surface in sufficient quantity to backfill the void volume 6' contained between the first and second particle layers. The applied binder solution is cured with another 15-30 minute cycle in the 70° C. oven. Additional layers of particles can be added in a likewise fashion.

Figure 5:
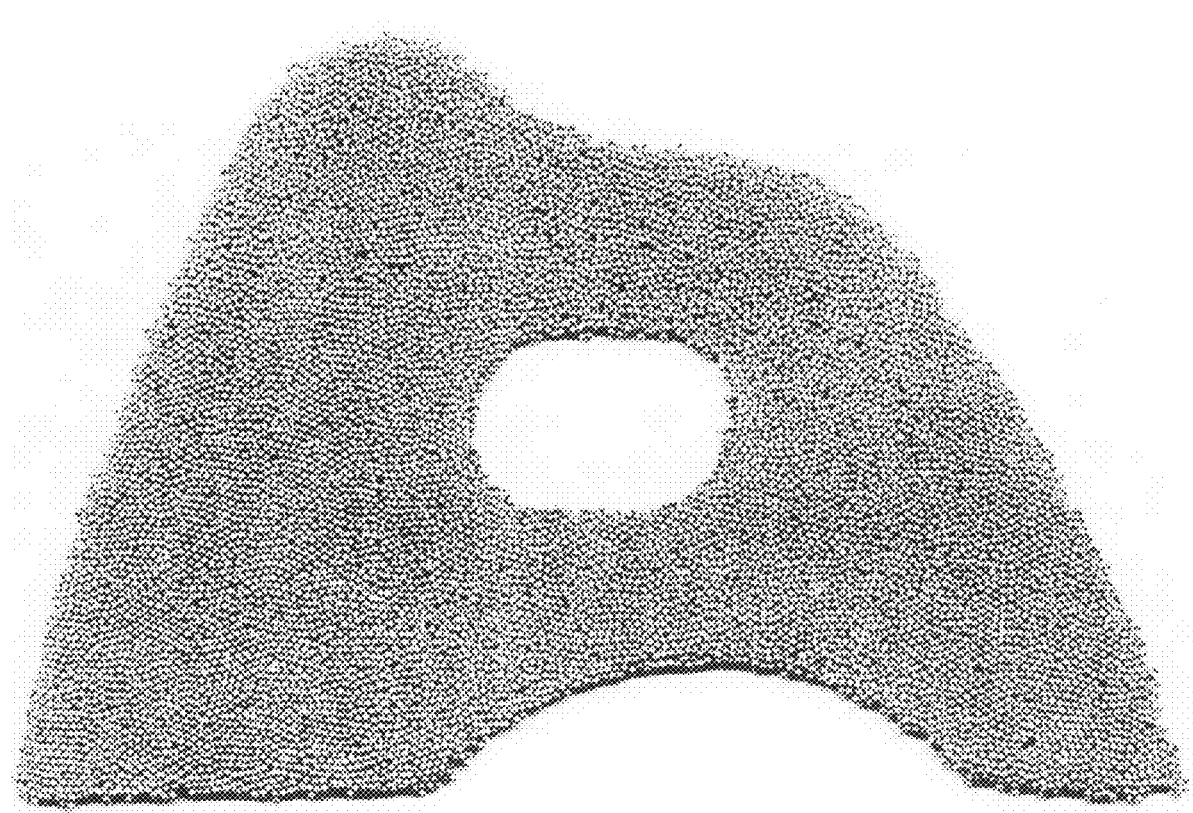
FIG. 5 is an image of a microstructure appliqué made in the shape of the section of the femoral knee component pictured FIG. 2 following the method of this invention.

After achieving the desired particle layer thickness, the cured appliqué is removed from the silicon rubber pad 2 by using a flat, wide blade inserted between the bottom-most particle layer and rubber pad to lift the piece from the pad. An image of a microstructure appliqué, fabricated according to the steps above in the shape corresponding to the section of the femoral knee component (pictured in FIG. 2), is shown in FIG. 5.

Once the microstructure appliqué is removed from the pad, it can be applied to the corresponding shaped area of the prosthesis by first adding a small amount of adhesive to the surface of the prosthesis and manually pressing the appliqué into the desired area. Alternatively, a pressure-sensitive adhesive film may be applied to the backside of the appliqué and then the appliqué pressed into place on the implant surface. The appliqué structure is permanently attached to the prosthesis surface through application of the appropriate sintering treatment.

A variety of biocompatible metals or metals having high strength and durability can be used to form microstructure appliqués. Exemplary materials include stainless steel, titanium, titanium alloys and cobalt-chromium alloys as well as other materials that are well known for use in the manufacturing of prosthetic implant articles. A particularly preferred metal alloy includes ASTM F-75.

The metal powder, which is used to make a microstructure appliqué of the present invention, can be a variety of different sizes, depending on the type and application of the implant device. Generally, the metal particles have a spherical geometry such as those made utilizing a rotating electrode process or plasma rotating electrode process, with the resulting product screened to achieve a narrow particle distribution. Generally, the particles can have a nominal diameter in the range between 0.007 to 0.033 inch. Choice of particle diameter and size distribution will determine the total volume of porosity and pore size distribution contained within the microstructure appliqué after permanent attachment to the prosthesis surface. A table showing the particle diameter and corresponding particle size in microns is shown in Table 1.

TABLE 1

Metal Particle Size Conversion Table

| Particle diameter (inch) | Converted to Microns(μ) |
|---|---|
| 0.0331 | 841 |
| 0.0280 | 707 |
| 0.0232 | 595 |
| 0.0197 | 500 |
| 0.0138 | 354 |
| 0.0098 | 250 |
| 0.0070 | 177 |

A preferred particle size distribution for manufacturing the porous coating on a prosthetic implant device includes particles in the range between 595 to 841 microns. Still another size distribution includes particles between 354 to 500 microns. Another narrow distribution includes particles between 250 to 354 microns. Finally, particles in the range between 177 to 250 microns are useful in creating a porous coating composed of smaller pores in comparison to the larger particle sizes.

A variety of binder solutions that have curing or solidifying properties, which firmly hold the particles together after reaching their respective endpoints, may be used. Example materials include aqueous solutions of methylcellulose and other water-soluble polymers such as polyvinyl alcohol. Fish gelatin, a natural substance harvested from the skins of codfish and sold as photoengraver's glue (Norland Products Inc., Cranbury, N.J.) is also suitable as a vaporizable binder in this application. These and others that are well known for use as binders, which dry and/or harden under specific conditions, may be applied in forming the microstructure appliqué.

This invention improves upon the method of manufacturing prosthetic implant devices containing porous metal-coated regions by making more uniform and reproducible structures in a multitude of shapes and thickness that is adaptable to automation. Although the invention is described with respect to an implantable knee femoral component, it is understood that the invention is applicable to the manufacture of other joint prostheses and implantable articles as well.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A method of forming a porous structure on a surface of a solid metallic material, comprising a prosthetic bone implant, wherein a microstructure appliqué of specific shape and thickness is assembled from metallic particles and vaporizable binder and affixed to the solid metallic material and permanently attached by application of appropriate sintering treatment, comprising the steps of:

a) dispensing metallic particles into a tray to form a single layer of uniformly, close-packed particles;
   b) preparing a pad in the shape of the area to be coated and adhesively securing the pad to a support block;
   c) applying an adhesive over the surface of the pad;
   d) pressing the adhesive-coated pad onto the packed layer of metallic particles in the tray;
   e) adding binder solution to fill the space in-between particles and the pad surface;
   f) curing the binder with application of appropriate heat; and g) recovering the microstructure appliqué from the pad and adhesively attaching to the surface of the solid metallic material in an area of similar shape.

2. The method of claim 1, including:
adjusting the thickness of the microstructure appliqué by adding successive particle layers by repeating steps c), d), e) and f).

3. The method of claim 1, including:
applying appropriate sintering treatment to remove cured binder and adhesive and permanently attaching the appliqué to the solid metallic material.

4. The method of claim 1 wherein the metallic particles are generally spherical in shape.

5. The method of claim 1 wherein the metallic particles in the tray are uniformly close-packed.

6. The method of claim 1 wherein the shaped pad is made of silicone rubber of suitable firmness.

7. The method of claim 2 wherein the metallic particles in the first layer of the microstructure appliqué and all successive layers are the same size and uniformly close-packed.

8. The method of claim 2 wherein the metallic particles in the first layer and all successive layers of the microstructure appliqué are from 595 to 841 microns in diameter.

9. The method of claim 2 wherein the metallic particles in the first layer and all successive layers of the microstructure appliqué are from 354 to 595 microns in diameter.

10. The method of claim 2 wherein the metallic particles in the first layer and all successive layers of the microstructure appliqué are from 250 to 354 microns in diameter.

11. A method in claim 2 wherein the metallic particles in the first layer and all successive layers of the microstructure appliqué are from 177 to 250 microns in diameter.

12. A method of forming a microstructure appliqué of specific shape and thickness for affixing to a surface of a prosthetic bond implant, comprising the steps of:
a) dispensing metallic particles into a tray to form a single layer of uniformly, close-packed particles;
b) preparing a pad in the shape of the area to be coated and adhesively securing the pad to a support block;
c) applying an adhesive over the surface of the pad;
d) pressing the adhesive-coated pad onto the packed layer of metallic particles in the tray;
e) adding binder solution to fill the space in-between particles and the pad surface;
f) curing the binder with application of appropriate heat;
g) adjusting the thickness of the microstructure appliqué by adding successive particle layers by repeating steps c), d), e) and f).

13. The method of claim 12 wherein the binder solution consists of an aqueous solution of fish gelatin.

14. The method of claim 12 wherein the binder solution consists of an aqueous solution of methylcellulose.

15. The method of claim 12 wherein the binder solution consists of a water-soluble polymer such as polyvinyl alcohol.

16. The method of claim 12 wherein the adhesive covering the pad surface is repositionable 75 spray adhesive.

* * * * *